United States Patent
Oakley et al.

(10) Patent No.: US 10,441,724 B2
(45) Date of Patent: Oct. 15, 2019

(54) DRIVE MECHANISM FOR A DELIVERY DEVICE

(71) Applicant: Sanofi, Paris (FR)

(72) Inventors: Tom Oakley, Cambridge (GB); Matt Schumann, Bourn (GB); Stuart Milne, Buckden St. Neots (GB)

(73) Assignee: Sanofi, Paris (FR)

( * ) Notice: Subject to any disclaimer, the term of this patent is extended or adjusted under 35 U.S.C. 154(b) by 922 days.

(21) Appl. No.: 14/904,736

(22) PCT Filed: Jul. 17, 2014

(86) PCT No.: PCT/EP2014/065337
§ 371 (c)(1),
(2) Date: Jan. 13, 2016

(87) PCT Pub. No.: WO2015/007818
PCT Pub. Date: Jan. 22, 2015

(65) Prior Publication Data
US 2016/0158456 A1    Jun. 9, 2016

(30) Foreign Application Priority Data

Jul. 17, 2013 (EP) .................... 13176881

(51) Int. Cl.
*A61M 5/315* (2006.01)
*A61M 5/20* (2006.01)
*A61M 5/31* (2006.01)

(52) U.S. Cl.
CPC .......... *A61M 5/31578* (2013.01); *A61M 5/20* (2013.01); *A61M 5/3146* (2013.01);
(Continued)

(58) Field of Classification Search
CPC .................... A61M 55/31578; A61M 5/31501
See application file for complete search history.

(56) References Cited

U.S. PATENT DOCUMENTS

| 4,865,591 A * | 9/1989 | Sams ................ A61M 5/31553 604/186 |
| 5,383,865 A | 1/1995 | Michel |

(Continued)

FOREIGN PATENT DOCUMENTS

| EP | 0 058 536 | 8/1982 |
| EP | 0 295 075 | 12/1988 |

(Continued)

OTHER PUBLICATIONS

Rote Liste, "50. Hypophysen-, Hypothalamushormone, andere regulatorische Peptide u. ihre Hemmstoffe," Chapter 50, ed. 2008, 20 pages.

(Continued)

*Primary Examiner* — Nathan R Price
*Assistant Examiner* — John A Doubrava
(74) *Attorney, Agent, or Firm* — Fish & Richardson P.C.

(57) ABSTRACT

A drive mechanism for a delivery device is presented. The drive mechanism comprises a housing (24) and a piston rod (6) having a longitudinal axis (x) and a piston rod feature (17). The drive mechanism further comprises a drive member (1) being movable with respect to the housing (24). The drive member (1) comprises a drive feature (15). The drive feature (15) is selectively engageable with the piston rod feature (17) by the radial displacement of the drive member (1) with respect to the piston rod (6). When the drive member (1) is in the first position, the drive member (1) is disengaged from the piston rod (6), and when the drive member (1) is in the second position, the drive feature (15) is engaged with the piston rod feature (17). When the drive member (1) moves distally with respect to the housing (24), said distal movement is transferred to the piston rod (6) such that the piston rod (6) moves distally with respect to the housing (24).

15 Claims, 7 Drawing Sheets

(52) U.S. Cl.
CPC .... *A61M 5/31535* (2013.01); *A61M 5/31541* (2013.01); *A61M 5/3157* (2013.01); *A61M 5/31501* (2013.01); *A61M 5/31543* (2013.01); *A61M 5/31553* (2013.01); *A61M 5/31561* (2013.01); *A61M 5/31573* (2013.01); *A61M 5/31583* (2013.01); *A61M 2005/3126* (2013.01); *A61M 2205/581* (2013.01); *A61M 2205/586* (2013.01)

(56) References Cited

U.S. PATENT DOCUMENTS

| | | |
|---|---|---|
| 7,699,815 B2 | 4/2010 | Langley et al. |
| 2008/0071227 A1 | 3/2008 | Moser et al. |
| 2011/0046565 A1 | 2/2011 | Radmer et al. |

FOREIGN PATENT DOCUMENTS

| | | |
|---|---|---|
| JP | 2001-513688 | 9/2001 |
| WO | WO 1995/021645 | 8/1995 |
| WO | WO 98/39041 | 9/1998 |
| WO | WO 2006/089734 | 8/2006 |

OTHER PUBLICATIONS

International Preliminary Report on Patentability in International Application No. PCT/EP2014/065337, dated Jan. 19, 2016, 11 pages.
International Search Report and Written Opinion in International Application No. PCT/EP2014/065337, dated Oct. 10, 2014, 13 pages.

\* cited by examiner

DRIVE MECHANISM FOR A DELIVERY DEVICE

CROSS-REFERENCE TO RELATED APPLICATIONS

This application is a U.S. national stage application under 35 USC § 371 of International Application No. PCT/EP2014/065337, filed on Jul. 17, 2014, which claims priority to European Patent Application No. 13176881.4, filed on Jul. 17, 2013, the entire contents of which are incorporated herein by reference.

The present disclosure relates to a drive mechanism for a delivery device, e.g. a drug delivery device such as an injector-type device and a drug delivery device.

Drug delivery devices are, for example, known from U.S. Pat. Nos. 5,383,865 A, 7,699,815 B2 and WO 2006/089734 A1.

It is an object of the present disclosure to provide an alternative or improved drive mechanism for a delivery device. Further, a drug delivery device should be provided.

This object is achieved by the subject-matter of the independent claims. Advantageous embodiments and refinements are subject-matter of the dependent claims.

One aspect of the present disclosure relates to a drive mechanism for a delivery device comprising a housing having a proximal end and a distal end. The drive mechanism further comprises a piston rod with a piston rod feature. The piston rod may have a longitudinal axis. The drive member is movable with respect to the housing, in particular in the axial direction and/or in the radial direction. The drive member comprises a drive feature. The drive member is further movable in the radial direction, e.g. perpendicular to the piston rod, between a first and a second position, wherein the drive feature is selectively engageable with the piston rod feature by the radial displacement of the drive member with respect to the piston rod. Preferably, the longitudinal axis extends through the proximal end and the distal end. The proximal and the distal end may be spaced apart from each other along the longitudinal axis. This embodiment provides the advantage that, depending on the engagement of drive feature and the piston rod feature, the piston rod may be moved or displaced by a corresponding movement of the drive member. Preferably, the piston rod and the drive member are arranged radially next to each other.

In an embodiment, the drive mechanism is configured such that when the drive member is in the first position, the drive member is disengaged from the piston rod and movable with respect to the piston rod. In this situation, the drive member may advantageously be axially moved with respect to the piston rod, preferably proximally for setting an amount of substance such as, e.g. a drug to be dispensed from the device and distally for decreasing or cancelling the set amount of substance, such that in a later step, the drive member may be (re-)engaged to the piston rod.

In an embodiment, the drive mechanism is configured such that, when the drive member is in the second position, the drive feature is engaged with the piston rod feature such that, when the drive member moves distally with respect to the housing, said distal movement is transferred to the piston rod and the piston rod moves distally with respect to the housing. According to this embodiment, it is achieved that further components of the drive mechanism may effect a movement of the piston rod via the drive member.

A further aspect of the present disclosure relates to a drug delivery device comprising the drive mechanism. Preferably, the piston rod is provisioned to advance a plunger or a piston which may be retained in a cartridge of the drug delivery device in the distal direction with respect to the cartridge such that drug which is contained in the cartridge may be dispensed from the drug delivery device. In an embodiment, the drive mechanism comprises a coupling element which is fixed to or formed integrally with the housing. The coupling element further comprises a plurality of axially spaced coupling features, each of which is configured to establish a unidirectional coupling with a piston rod feature such that a proximal movement of the piston rod with respect to the housing is prevented. The prevention of the proximal movement of the piston rod increases the safety of the drug delivery device, as the piston rod or the device is prevented from being reset and/or misused.

In an embodiment, when one of the coupling features establishes the unidirectional coupling, another one of the coupling features does not establish the unidirectional coupling, wherein the coupling features and the piston rod feature are configured such that the unidirectional coupling is formed by means of different coupling features depending on the relative position of the piston rod and the coupling element. According to this embodiment, a movement of the piston rod with respect to the coupling element at comparably small incremental steps may be carried out, whereby the unidirectional coupling may be embodied at comparatively large dimensions.

In an embodiment, the piston rod feature comprises a set of teeth being arranged and configured to be engageable with the coupling features. This embodiment allows an engagement of the piston rod with the drive feature and/or the coupling features which is dependent on the direction of relative movement. Preferably, the teeth of the piston rod are provided along the whole or almost the whole axial length of the piston rod. The teeth of the piston rod may be equidistantly disposed, preferably in the axial direction, along the piston rod.

In an embodiment, each of the coupling features comprises at least one tooth arranged and configured to be engageable with the teeth of the piston rod feature. The axial space between two coupling features is chosen such that a distal end face of the tooth of a first coupling feature abuts a proximal end face of a first tooth of the piston rod feature. This coupling feature then establishes the unidirectional coupling of the piston rod with respect to the housing.

In an embodiment, the piston rod is movable by a distance which is smaller than the distance A between the proximal end faces of two adjacent teeth of the piston rod feature.

In an embodiment, a movement of the piston rod with respect to the coupling element is carried out at incremental steps which are smaller than the distance A.

In an embodiment, the piston rod does not rotate.

In an embodiment, the distance D between a distal end face of the tooth of a second coupling feature and a proximal end face of a second tooth of the piston rod feature is smaller than the distance A between the proximal end faces of two adjacent teeth of the piston rod feature. Expediently, this embodiment facilitates a movement of the piston rod with respect to the coupling element to be carried out at incremental steps which are smaller than the distance A, such that the teeth of the piston rod may be spaced by distances greater than the minimum distance by which the piston rod is moved. Thereby, a manufacture of said teeth may be kept cost-effective. Furthermore, particularly small amounts of substance may be delivered in this way.

In an embodiment, the drive mechanism is configured such that when the piston rod is moved distally by the distance D with respect to the housing, the first tooth of the piston rod feature is moved out of abutment from the tooth of the first coupling feature and the proximal end face of the second tooth of the piston rod feature abuts the distal end face of the tooth of the second coupling feature, In an embodiment, the distance D corresponds to a minimum amount of a substance which can be dispensed from the delivery device.

In an embodiment, the drive feature comprises a plurality of axially spaced drive features and each drive feature comprises at least one tooth being configured and arranged to be engageable with the teeth of the piston rod feature. The drive features and the piston rod feature are arranged and configured such that, when the drive member is in the second position, a distal end face of a tooth of one of the drive features abuts a proximal end face of a tooth of the piston rod feature and a distal end face of a tooth of another drive feature is spaced by the distance D' from a proximal end face of a tooth of the piston rod feature, wherein the distance D' corresponds to the minimum amount of a substance which can be dispensed from the delivery device. According to the embodiment, it is assured that at least one of the drive features effectively abuts or engages a tooth of the piston rod feature, when the drive member is in the second position such that the minimum amount of the substance can be dispensed.

In an embodiment, the drive mechanism is configured such that in a setting mode of operation, the drive member is in the first position and in a dispensing mode of operation, the drive member is in the second position.

In an embodiment, the drive mechanism comprises a dose member and the drive mechanism is configured such that in a setting mode of operation, the drive member is in the first position and in a dispensing mode of operation, the drive member is in the second position. In the setting mode of operation, the drive member is expediently free to move axially with respect to the piston rod, particularly in the proximal and/or distal direction. In the dispensing mode of operation, the drive member expediently transfers movement to the piston rod such that substance may be dispensed from the delivery device.

In an embodiment, in the setting mode of operation, the dose member is rotatable in a first direction with respect to the housing to set a dose and in the dispensing mode of operation, the dose member is rotatable in a second direction opposite to the first direction with respect to the housing to dispense a set dose.

In an embodiment the drive mechanism is configured such that the rotation of the dose member with respect to the housing is converted into an axial movement of the drive member with respect to the piston rod. According to this embodiment, the drive mechanism can, for example, be embodied space-saving and robust. Moreover, in this way, the drive mechanism may be embodied with a low number of interacting parts and with a torsion spring in order to drive the piston rod. In the setting mode of operation, the drive member may be moved distally or proximally. When the set dose is increased, the drive member is, preferably, moved proximally, When the set dose is decreased, the drive member is, preferably, moved distally, In the dispensing mode of operation, the drive member may be moved distally but preferably not moved proximally.

In an embodiment, the dose member and the drive member are threadedly coupled with respect to each other. With this embodiment, the conversion of rotation of the dose member into an axial movement of the drive member is achieved most expediently. Preferably, the threaded coupling between the dose member and the drive member is configured such that the threaded interaction is not affected by the radial displacement the drive member experiences with respect to the piston rod and the dose member. To this effect, the thread coupling may comprise a certain radial play.

In an embodiment, either on the dose member or on the drive member, a threaded shaft may be provided which is elastic to a certain extent, for example in a direction perpendicular to the longitudinal axis. Said threaded shaft may rotate about the longitudinal axis or an axis parallel to the longitudinal one. The dose member may comprise an outer thread which matches an inner thread of the drive member.

In an embodiment, the drive mechanism comprises a drive spring which is coupled to the dose member. The drive spring is arranged and configured such that, when the dose member rotates in a first direction with respect to the housing, the drive spring is loaded or biased, and wherein in the dispensing mode of operation, the drive spring drives the rotation of the dose member in a second direction with respect to the housing. According to this embodiment, the drive mechanism can be embodied semi-automatic, whereby a biasing of the drive spring during setting, e.g. by way of a user of the drive mechanism, may provide some or all of the energy required to drive the piston rod or, as the case may be, to dispense a substance from the delivery device. The drive spring may be a torsion spring.

In an embodiment, the drive mechanism comprises a releasable clutch mechanism, wherein the releasable clutch mechanism is configured such that in the setting mode of operation, the releasable clutch mechanism is engaged and the dose member is selectively rotationally locked with respect to the housing against a spring force of the drive spring. Thereby, it is achieved that a dose can be set by the drive mechanism, as the drive spring may be locked and prevented from back-rotation and/or relaxation after a dose has been set. Preferably, when the dose member is selectively rotationally locked with respect to the housing against the spring force, the dose member may still be rotated during setting of another dose or cancelling or decreasing of a dose by the user. The force applied by the user in this respect may be greater than a driving force of the drive spring. The driving force may be the force exerted by the drive spring to the piston rod.

In an embodiment, in the dispensing mode of operation, the releasable clutch mechanism is released and the dose member is rotated by the drive spring with respect to the housing. According to this embodiment, the driving force of the drive spring may be exploited to drive the piston rod within the cartridge and to dispense a dose of drug from the drug delivery device.

The releasable clutch mechanism is configured to be manually operable, i.e. engagable and releasable by the user. Preferably, the clutch mechanism is configured to be engaged and/or released just by the physical strength of the user's hand. According to this embodiment, further auxiliary means are not needed when the user operates the releasable clutch mechanism.

In an embodiment, the drive mechanism comprises an actuation member and a displacement member, wherein the actuation member is configured to interact with the displacement member such that when, in the setting mode of operation, an axial movement of the actuation member is transferred to a radial movement of the displacement member with respect to the piston rod, it is switched from the setting mode to the dispensing mode of operation, whereby the drive member moves from the first to the second position. Upon a depressing of the actuation member, the displacement member is preferably at least partly moved axially. The actuation member may further be configured such that the user may rotate or depress the actuation member with respect to the housing in order to set or dispense a dose of drug, respectively. The actuation member may be a dose button of the drive mechanism or the drug delivery device.

In an embodiment, the displacement member is rotationally locked with respect to the housing and the displacement member comprises a clutch feature wherein, in the setting mode of operation, the displacement member is axially moved with respect to the dose member, thereby releasing the releasable clutch mechanism. With this embodiment, the releasable clutch mechanism can be embodied most expediently. The clutch feature may be splined to the dose member via a tooth engagement. To this effect, the clutch feature may comprise a tooth or a pin and the dose member may comprise a pinion or a gear to which the tooth or pin may be engageable. Said tooth or pin may be embodied as a protrusion protruding from a main body of the displacement member. Alternatively, the drive mechanism may be configured such that the protrusion is provided on the dose member.

In an embodiment, the drive mechanism comprises a guide feature which is axially fixed to or formed integrally with the housing. The guide feature and the displacement member are arranged and configured such that an axial movement of the displacement member with respect to the housing is at least partially converted into a radial movement of the displacement member with respect to the piston rod, wherein the displacement member interacts with the drive member such that when the displacement member moves radially with respect to the piston rod, the drive member is displaced with respect to the piston rod from the first to the second position. According to this embodiment, it is simply achieved that a radial component of movement of the displacement member is provided without requiring further features or mechanisms of the drive mechanism.

Features which are described herein above and below in conjunction with different aspects or embodiments may also apply for other aspects and embodiments. Particularly, features described with respect to the arrangement may apply for the method, the unit and the module and vice versa.

Further features and advantages of the subject matter of this disclosure will become apparent from the following description of the exemplary embodiment in conjunction with the figures, in which:

FIG. 3a shows a situation in which a clutch mechanism is engaged and FIG. 3b shows a situation in which the clutch mechanism is disengaged.

Figure 1:
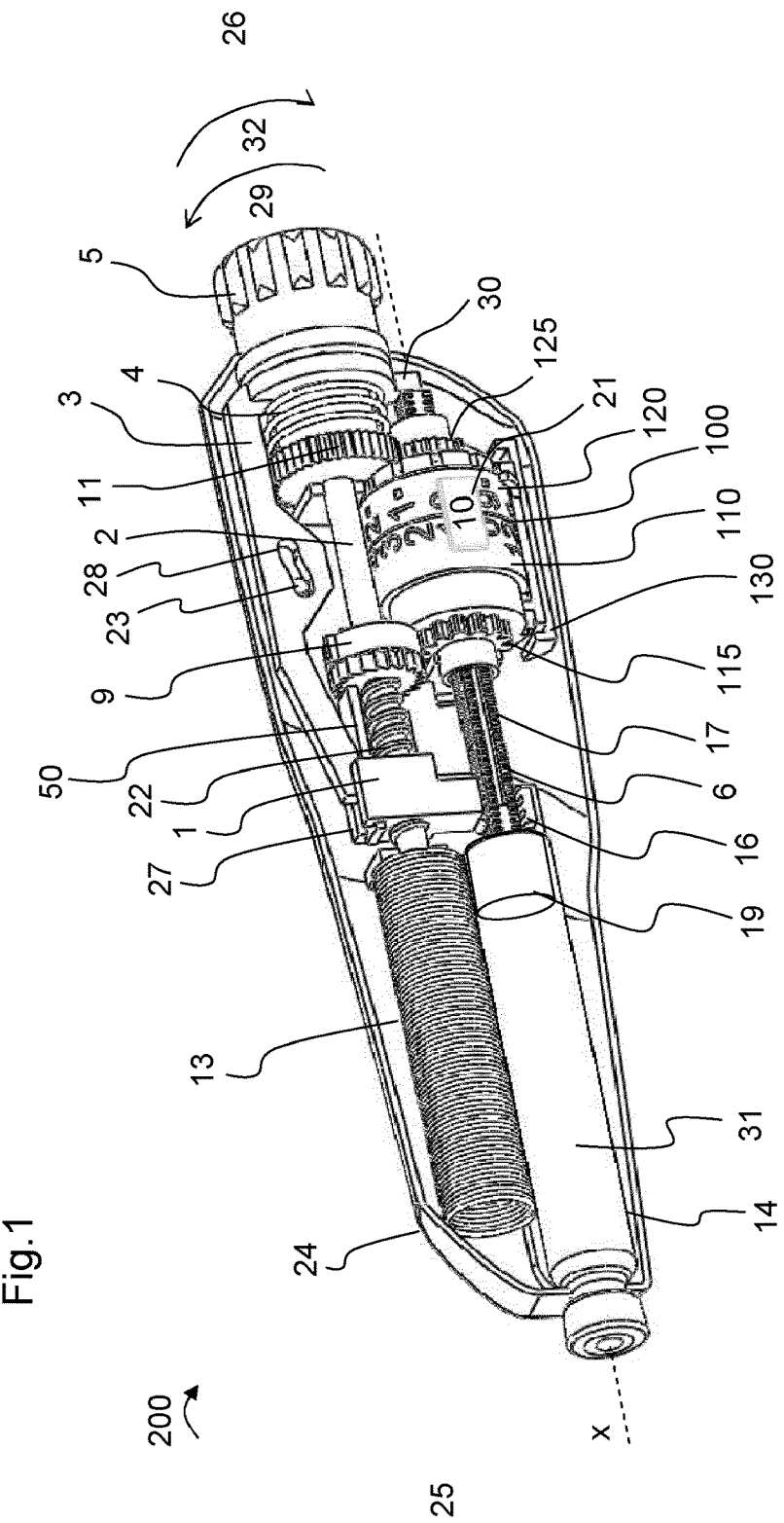
FIG. 1 shows a perspective view of components of a drug delivery device.

Like elements, elements of the same kind and identically acting elements may be provided with the same reference numerals in the figures. Additionally, the figures may be not true to scale. Rather, certain features may be depicted in an exaggerated fashion for better illustration of important principles.

FIG. 1 shows a perspective view of a drug delivery device 200. The drug delivery device may be a disposable drug delivery device. The drug delivery device 200 comprises a housing 24 which houses further components. Only one half of the housing 24 is shown in FIG. 1 such that inner components of the drug delivery device 200 are visible. The drug delivery device 200 further comprises a drive member 1 and a piston rod 6. The piston rod may have a cross-section resembling a square, rectangle, parallelogram, circle or ellipse.

The drive member 1 is configured to move the piston rod 6 in a distal direction, e.g. during a dose delivery of the drug delivery device 200. The drug delivery device 200 comprises a longitudinal axis x, a distal end 25 and a proximal end 26. Preferably, the longitudinal axis x extends through the distal end 25 and the proximal end 26. In other words, the distal end 25 and the proximal end 26 may be spaced along the longitudinal axis. The drug delivery device 200 further comprises a, preferably replaceable, cartridge 14 in which a plunger 19 is retained. The piston rod 6 may be arranged next to or abut the plunger 19. The cartridge 14 may further contain a drug 31 or medical substance to be dispensed from the drug delivery device 200. The drug 31 may be dispensed in measured doses. The drug 31 may be retained in the cartridge 14. The cartridge 14 may contain 1.5 ml or 3 ml of the drug 31. Preferably, the cartridge 14 is arranged or aligned longitudinally. The piston rod 6 may also be arranged or retained longitudinally such that it is movable with respect to the cartridge 14. The drug delivery device 200 further comprises a dose member 2 which may effect a dose setting and a dose dispensing of the drug delivery device 200. The dose member 2 is threadedly engaged with the drive member 1, e.g. via an outer thread 22. Accordingly, the drive member 1 may comprise an inner thread matching with the outer thread 22. Thereby, said threaded engagement may be configured such that during a rotation of the dose member 2 with respect to the housing 24, the drive member 1 is axially moved. In a setting mode of operation, the dose member is rotatable in a first or second direction with respect to the housing to set a dose and in a dispensing mode of operation, the dose member 2 is rotatable in a second direction opposite to the first direction with respect to the housing to dispense a set dose. The drug delivery device 200 further comprises a displacement member 3 which may be configured to displace or to contribute to the displacement of the drive member 1.

The dose member 2 and the displacement member 3 are preferably aligned parallel to the longitudinal axis x but arranged radially offset from the cartridge 14 and the piston rod 6. Drive member 1 may at least partially be arranged between the piston rod 6 and the dose member 2. A longitudinal axis of the drive member may thereby be aligned radially. The dose member 2 and the displacement member 3 may comprise an elongate shape, respectively. The displacement member 3 is engaged to the drive member 1 via a guidance 27 of drive member 1. The guidance 27 may be configured such that, e.g., when the dose member 2 is rotated, the drive member 1 is rotationally locked with respect to the displacement member 3 such that the dose member 2 and the drive member 1 are rotated relative to each other. The drug delivery device 200 further comprises a spring element 4 and a dose button 5. The spring element 4 is retained between a pinion 11 of the dose member 2 and the dose button 5. The displacement member 3 comprises a drive member displacement member 50 which comprises an elongate shape and which is aligned parallel to the longitudinal axis x. The length of the drive member displacement member 50 may relate to the travel of the drive member 1 and in this way to the amount of drug 31 to be dispensed during the dispensing of drug from the filled cartridge. The drive member displacement member 50 is retained by the guidance 27. Preferably, the guidance 27 rotationally and radially locks the drive member displacement member 50, whereby only relative axial movement of said components is allowed.

The displacement member 3 comprises a rod displacement feature 30. In the depicted situation, the drug delivery device 200 is in an initial state. During the first use of the drug delivery device 200, the rod displacement feature 30 may abut the piston rod 6.

The drug delivery device 200 further comprises an indication assembly 100. The indication assembly 100 comprises a first indication member 110 and a second indication member 120. The piston rod 6 extends through the first and the second indication members 110, 120. The indication assembly 100 further comprises a locking member 130 which is configured to rotationally lock the first and the second indication member 110, 120 with respect to the housing 24. The drug delivery device 200 further comprises a guide feature 23 which is fixed to the housing 24. When, e.g. the dose button 5 is moved distally, the displacement member 3 is also moved distally against the resilience of the spring element 4. Thereby, the displacement member 3 is guided by the guide feature 23 which is engaged to a bore 28 of the displacement member 3. Via the bore 28 and the guide feature 23, an axial movement of the displacement member 3 may at least partly be converted into a radial movement of the displacement member 3 and/or the drive member displacement member 50. The displacement member 3 may comprise a certain flexibility.

The drug delivery device 200 further comprises a drive spring 13 which is configured such that it is loaded upon a rotation of the dose member 2 in a first direction (cf. arrow 29). To this effect, a distal end of the drive spring 13 is preferably fixed to the housing 24 and a proximal end of the drive spring 13 is preferably fixed to, e.g. a distal end of the dose member 2. The drive spring 13 is a torsion spring. During setting of a dose of drug 31, the drive spring 13 is loaded and spring energy is stored which can be used for a delivery of the drug 31. The displacement member 3 is rotationally locked with respect to the housing 24. In the setting mode of operation, the dose button 5 is rotated in the first direction 29. The dose button 5 is connected to the dose member 2, wherein said connection is configured such that the dose member 2 is also rotated in the first direction along with the dose button 5, such that the drive spring 13 is loaded. Due to the threaded engagement of the dose member 2 and the drive member 1, in the setting mode of operation, the drive member 1 is moved proximally while in the dispensing mode of operation, the drive member 1 is moved distally. In the setting mode of operation, the dose button 5 may also be rotated in a second direction (cf. arrow 32) opposite to the first direction 29 in order to decrease or cancel a set dose of drug 31. This would move drive member 1 distally. The dose button may be operated, e.g. rotated to dial the size of a dose to be delivered. The size may span a range between zero units and a maximum number of gradations or units, e.g. 120.

The displacement member 3 and the dose member 2 are coupled via a releasable clutch mechanism by which said components are rotationally lockable. The releasable clutch mechanism is configured to withstand the spring force of the drive spring when a dose is set. When a maximum settable dose is set, the releasable clutch mechanism has to withstand a maximum spring force. The releasable clutch mechanism can be released by distal movement or depressing of the dose button 5 with respect to the housing 24. Thereby, the displacement member 3 and the dose member 2 are disengaged (cf. FIG. 3 further below).

The spring element 4 biases the releasable clutch mechanism towards the engaged state. In the setting mode of operation, the drive member is preferably in a first position, wherein it is disengaged from the piston rod 6. When the dose button 5 is depressed or moved distally which is preferably manually performed by a user of the drug delivery device 200, it is preferably switched from the setting mode to the dispensing mode of operation. During distal movement of the dose button 5 and the displacement member 3 with respect to the housing 24, the displacement member 3 is guided via the guide feature 23 in such a manner that the displacement member 3 displaces the drive member 1 radially, i.e. towards the piston rod 6 such that the piston rod 6 is displaced from the first to a second position. In the second position, the drive member 1 is engaged to the piston rod 6. The drive mechanism is preferably configured such that at the same time or slightly after the drive member 1 has engaged the piston rod, the releasable clutch mechanism is released and the spring force of the loaded drive spring 13 drives the dose member 2 such that the dose member 2 is rotated in the second direction 32. The drive spring 13 is preferably configured to provide for a sufficient spring force for a minimum dose of drug 31 to be dispensed from the drug delivery device 200 when the piston rod 6 is in the second position. Due to the threaded interaction of the dose member 2 and the drive member 1, the drive member 1 is moved distally with respect to the piston rod 6 when the dose member 2 rotates. The piston rod 6 comprises a piston rod feature 17 and the drive member 1 comprises a drive feature 15 (cf. FIG. 2). By an engagement of the drive feature 15 with the piston rod feature 17, a distal movement of the drive member 1 may be transferred to the piston rod 6 such that the piston rod 6 is moved distally with respect to the housing 24. Consequently, the plunger 19 is moved distally inside the cartridge 14 in order to dispense drug 31 from the drug delivery device 200. The drug delivery device 200 further comprises a coupling element 16 which is configured such that the piston rod 6 is prevented from being moved in the proximal direction. When the dose button 5 is released either during or after a dispensing operation, the releasable clutch mechanism is reengaged and the drive member 1 is moved back from the second into the first position thus switching the drive mechanism back into the setting mode of operation. The drug delivery device 200 may be an injector-type device comprising a needle or a needle assembly (not explicitly indicated) which may be provided at the distal end 25. Furthermore, the drug delivery device 200 may comprise a cap (not explicitly indicated) to cover the distal end 25. The dose button 5 may need to be rotated six times during setting of a dose. This may correspond to a set dose of 120 units of drug 31 to be dispensed.

In the following, a priming mechanism is described by which the drug delivery device 200 may be switched from an initial state to a primed state. In the initial state, the drug delivery device 200 is preferably in an as-fabricated or as-assembled state, wherein the dose button 5 has not yet been actuated or pressed. Then, the cartridge 14 preferably contains an initial amount of drug 31. The rod displacement feature 30 is axially movable between a first position and a second position. In the initial state, the piston rod 6 and the rod displacement feature 30 are arranged such that some or all of the movement of the rod displacement feature 30 from the first position to the second position is transferred to the piston rod 6 such that the piston rod 6 is moved with respect to the cartridge 14. In the primed state, axial movement of the rod displacement feature 30 from the first position to the second position is not transferred to the piston rod 6. Particularly, when the dose button 5 is in the initial state, a proximal face 47 of the piston rod 6 and a distal face 46 of the rod displacement feature 30 preferably abut (cf. also FIG. 6). Alternatively, the distance between the proximal face 47 of the piston rod 6 and a distal face 46 of the rod displacement feature 30 is at least smaller than the distance between the first and the second position. When, in the initial state, the dose button 5 is pressed by the user for the first time, the rod displacement member 30 is moved axially, thereby moving or advancing the piston rod 6 distally with respect to the cartridge 14. Expediently, a needle is provided which in turn provides fluid communication between the interior of the cartridge 14 and the outside. The dose button 5 is moved until the rod displacement feature 30 is arranged in the second position, whereby an initial static friction force between the plunger 19 and the cartridge 14 is overcome. Thereby, the drug delivery device 200 is primed. The priming operation may additionally comprise the removal of clearances and/or tolerances and the application of compression or tension to further device components such that the device is prepared for an operation with no or only a minimum play between elements of the drive mechanism. The use of force transferred from the rod displacement member 30 to the piston rod 6 may help the drive mechanism to overcome initial static friction forces, particularly between the plunger 19 and the cartridge 14.

In the primed state, the driving force is preferably sufficient to move or advance the piston 19 distally with respect to the cartridge 14. As an advantage, the drive spring 13 may be designed smaller and more efficient with respect to costs and space requirements. In the initial state, the distance between the piston rod 6 and the rod displacement feature 30 is preferably greater than a manufacturing tolerance of the cartridge 14 and/or the piston rod 14. Thereby, it is assured, that the direct distal movement of the rod displacement feature—which is effected manually by the user—is effectively transferred to the piston rod 6. Preferably, the plunger 19 and the cartridge 14 are configured such that the initial static friction force takes values between 10 N and 20 N. Preferably, the mentioned drive mechanism is configured such that the driving force takes values between 3 N and 10 N.

The distance by which the dose button 5 is depressed may be 3 to 4 mm. The rod displacement feature 30 may be moved axially between the first and the second position. The distance the rod displacement feature 30 is moved axially may be 2 mm. Additionally, there may be a play or clearance of distance B of 1 to 2 mm between the dose button 5 and the displacement member 3 (cf. FIG. 6). To this effect, a further biasing member (not explicitly indicated) may be provisioned which tends to separate the mentioned components accordingly.

An advantage of the described priming functionality pertains to the effect that once the drug delivery device 200 is primed, the user may repeat the actuation or depressing of the dose button 5 if he is not sure about the state of the device. By means of the force necessary to depress the dose button 5, the user will immediately realize whether the device has already been primed or not. Thereby, it is contributed to a simple and safe operation of the drug delivery device 200. The presented drug delivery device 200 provides the advantages of, for instance, a comfortable, user-friendly shape, a low injection force owing to the priming mechanism, semi-automatic injection and the possibility to assemble the drug delivery device in an easy way. Moreover, the drug delivery device may be easily distinguished from other devices due to its characteristic shape. That is to say, the shape of the drug delivery device may deviate slightly from a cylinder-like shape which is usual for similar drug delivery devices. To this effect, it may be easier to hold it in the palm of the user's hand and/or to operate the drug delivery device.

Figure 2A:
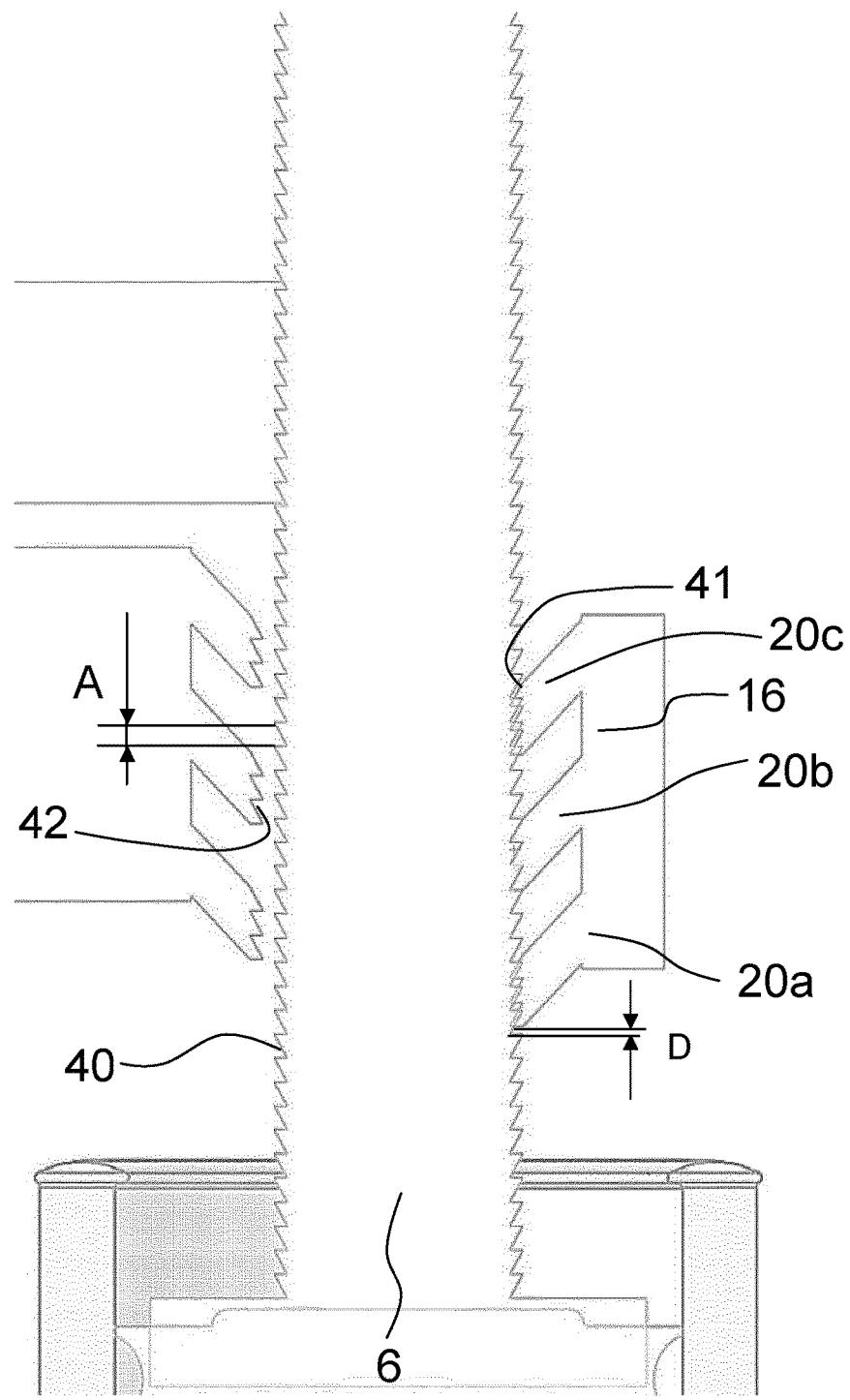
FIGS. 2a to 2c show the schematics of a side view of components of a drive mechanism for a drug delivery device.
Figure 2B:
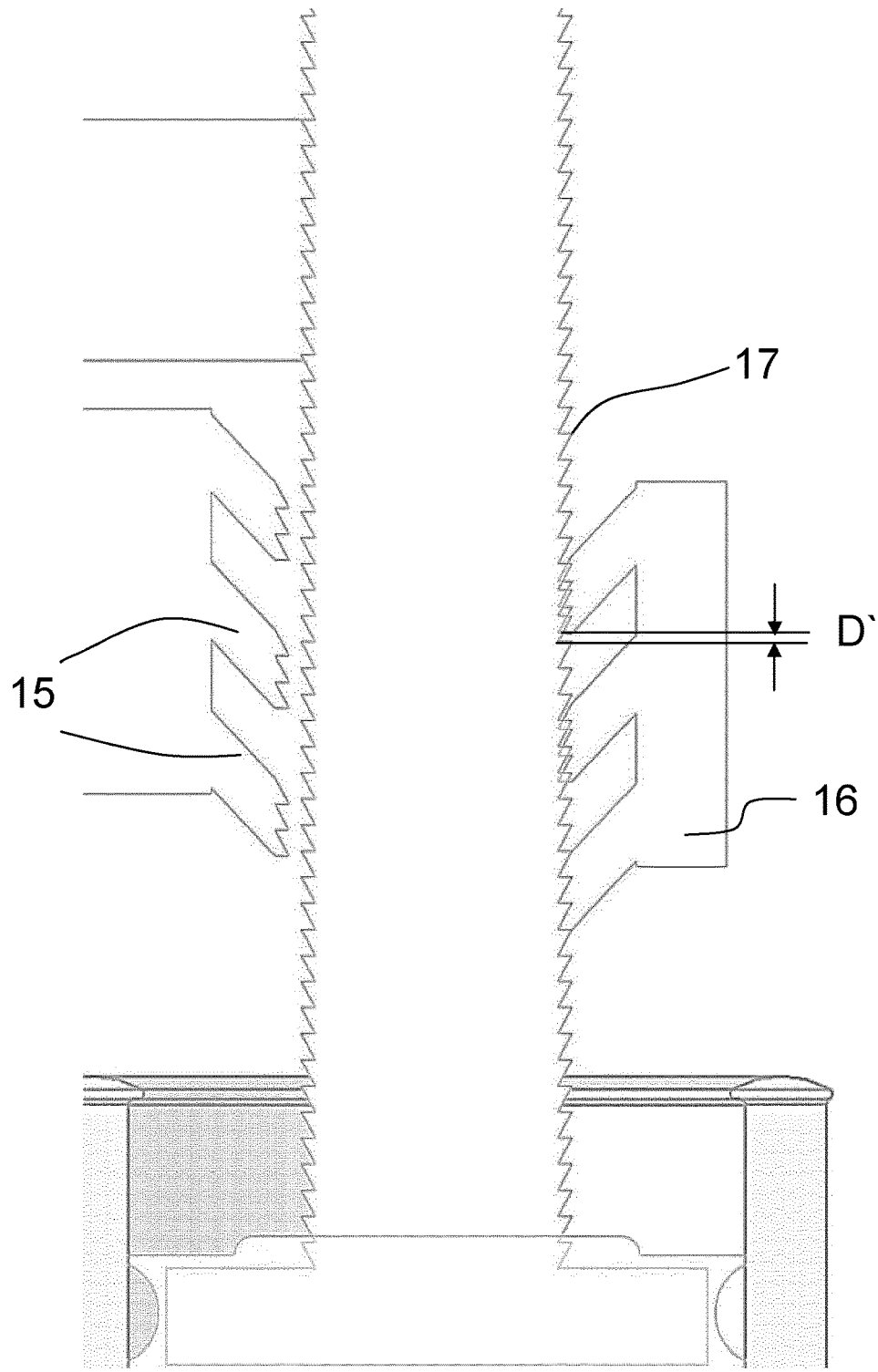
Figure 2C:
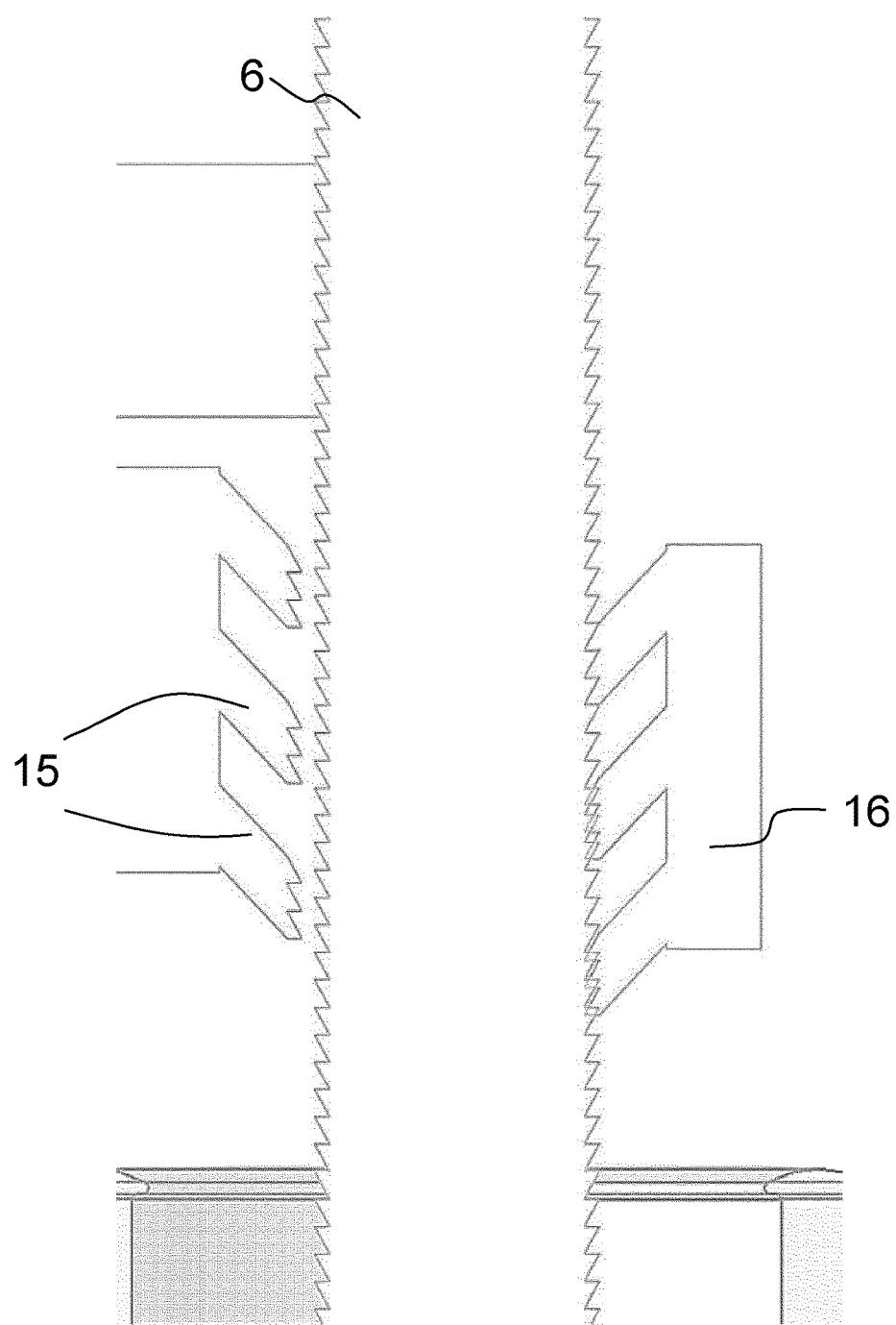

FIG. 2 illustrates a coupling between the piston rod 6 and the coupling element 16 by means of the FIGS. 2a to 2c. Drive feature 15 of the drive member 2 may constitute a plurality of drive features 15 which are shown each with a tilt towards the distal end 25. The depicted situation respectively relates to the setting mode of operation, wherein the drive features 15 are disengaged from the piston rod 6. The coupling element 16 is preferably fixed to or integrally formed with the housing 24. The coupling element 16 comprises three axially spaced coupling features 20 each of which comprises teeth 41. The coupling features 20 are also tilted towards the distal end 25. The piston rod 6 comprises a set of teeth 40 which exhibit the piston rod feature 17. The teeth 40 are configured uniformly and arranged equidistantly. Furthermore, the teeth 40 may be arranged at an inwardly directed, as well as an outwardly directed side surface of the piston rod 6. The side surfaces of the piston rod 6 may be flat or non-flat, such as even. Each of the coupling features 20 is configured to establish a unidirectional coupling with the teeth 40 such that a proximal movement of the piston rod 6 with respect to the housing 24 is prevented. In FIG. 2a, only the coupling feature 20b in the middle establishes said unidirectional coupling, as proximal end faces of the teeth 40 abut distal end faces of teeth 41 of that coupling element while this is not the case for the other coupling features 20b, c. The distance between the proximal end faces of two adjacent teeth 40 of the piston rod 6 is indicated by A. The axial distance between the coupling features 20 is chosen such that the distance D between a distal end face of a tooth 41 of the coupling feature 20c which does not establish the unidirectional coupling and a proximal end face of a tooth 40 of the piston rod 6 feature is smaller than the distance A. Preferably, the distance D corresponds to a minimum amount of a drug 31 to be dispensed from the delivery device 200. The distance D is preferably defined by those teeth 42 of the piston rod 6 which are arranged proximally next to the respective tooth 41 of the respective coupling element. The distance D corresponding to a minimum amount of a drug 31 to be dispensed is expediently smaller than the distance A. Consequently, the piston rod 6 may be moved distally with respect to the coupling element 16 by a distance smaller than the distance A. In FIG. 2b, as compared to the FIG. 2a, the piston rod 6 has been moved distally (to the left) with respect to the coupling element 16 by the distance D. Thereby, the proximal end faces of the teeth 40 of the piston rod 6 have been moved out of abutment with the distal end faces of the teeth 41 of the middle coupling feature 20b and proximal end faces of the teeth 40 abut distal end faces of the left coupling feature 20a such that only this coupling feature establishes unidirectional coupling to the piston rod 6. In FIG. 2c, the piston rod 6 has been moved further axially by the distance D', as compared to FIG. 2b. As a consequence, only the right coupling feature 20c forms the mentioned unidirectional coupling to the piston rod 6. The distance D' may relate to the distance D.

The drive features 15 of the drive member 1 are axially spaced, wherein each drive feature 15 comprises teeth 42 being configured to be engagable with the teeth 40 of the piston rod 6, wherein the drive features 15 and the teeth 42 are configured such that when the drive member 2 is in the second position, a distal end faces of a teeth 42 of one of the drive features 15 abut proximal end faces of teeth 40 of the piston rod 6 and distal end faces of a teeth 42 of another drive feature 15 are spaced preferably by the distance D from proximal end faces of a teeth 40 of the piston 6.

The functionality which is described herein by means of three teeth 41 may also function with coupling features and drive features which only comprise one tooth each. However, the provision of a plurality of teeth adds greater strength and some redundancy in the case of failure.

Figure 3A:
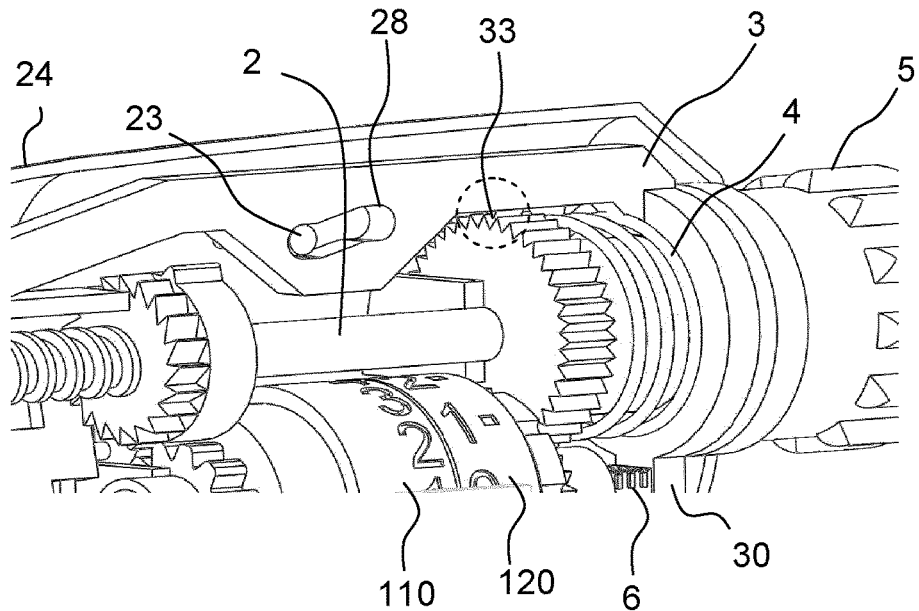
FIGS. 3a and 3b show a partial perspective view of components of the drug delivery device.
Figure 3B:
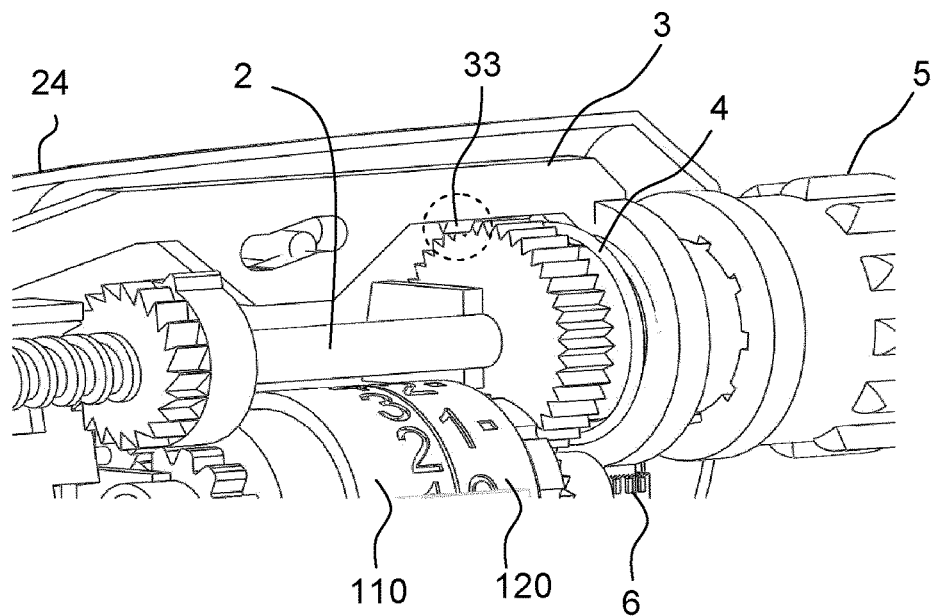

FIG. 3a shows a partial perspective view of inner components of the drug delivery device 200 in the setting mode of operation. The displacement member 3 comprises a clutch feature 33 which is, in the depicted situation, engaged to the pinion 11 of the dose member 2. In this situation, the releasable clutch mechanism is engaged. The pinion comprises teeth 48. The clutch feature 33 is a tooth-like clutch feature which is engaged or splined to the teeth 48 (cf. dashed circle). Although the dose member 2 may be selectively rotationally locked with respect to the housing 24 against the spring force of the drive spring 13, it may still be rotated, e.g. by a rotation of the dose button 5 with respect to the housing 24 which is performed by the user. During a setting operation, particularly during a clockwise rotation (cf. arrow 29 in FIG. 1) of the dose member 2 with respect to the displacement member 3, said clutch interaction between the clutch feature 33 and the pinion 11 may be overcome by the user. The torque required to set a dose may be 13.4 mNm for a set dose of zero and 25.4 mNm for a set dose of 120 units. The torque required to decrease or cancel a dose may be 16.8 mNm for a minimum dose and 4.8 mNm for the maximum settable dose. Expediently, said torques are larger than the torque which is applied to the dose member 2 by the drive spring 13. FIG. 3b shows the situation in the dispensing mode of operation, wherein the clutch feature 33 has been disengaged from the teeth 48 of the pinion 11, by movement of the dose button 5 with respect to the housing 24. As compared to FIG. 3a, also the displacement member 3 has been moved distally with respect to the dose member 2. Consequently, in FIG. 3b, the dose member 2 is free to rotate with respect to the displacement member 3. In this situation, it is enabled that the drive spring 13 drives the dose member 2 in the second direction or counter clockwise (cf. arrow 32 in FIG. 1) by rotation.

Figure 4:
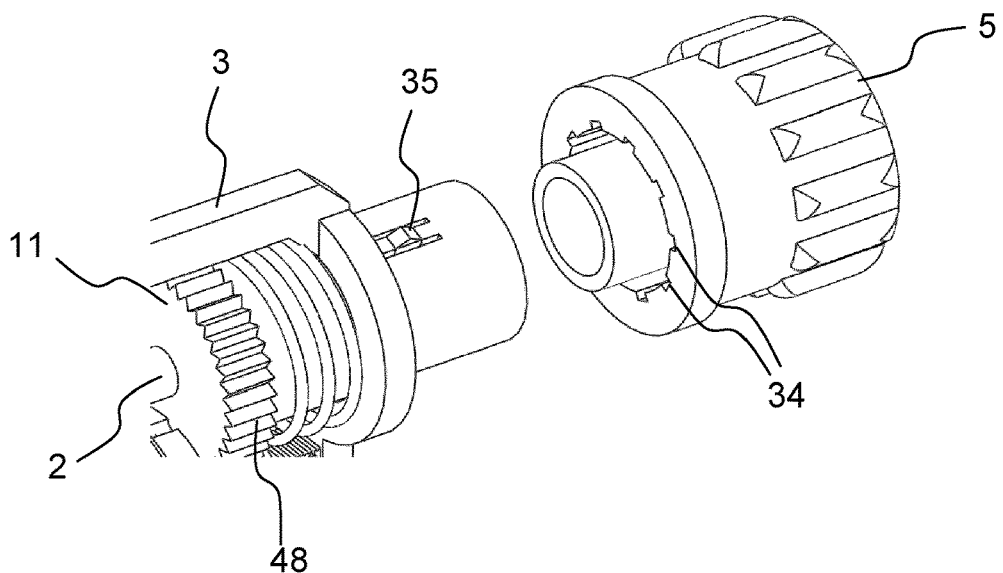
FIG. 4 shows a perspective view of components of the drug delivery device.

FIG. 4 shows parts of components of the drug delivery device 200 near the proximal end 26. In the setting mode of operation, the dose button 5 is rotationally locked to the dose member 2 by a dose member spline 35 which is retained in a recess 34 of the dose button 5 such that the dose member 2 is rotated along with the dose button 5. In the dispensing mode of operation, the dose member 2 is free to rotate with respect to the dose button 5. To this effect, the dose member spline 35 and the recesses 34 are configured such that when the dose button 5 is moved distally with respect to the dose member 2, e.g. during a dispensing operation, the dose member spline 35 is disengaged from the corresponding recess 34 and the dose member 2 is free to rotate with respect to the dose button 5. When the dose button 5 is released again, e.g. during or after a dispensing operation, the dose member spline 35 is reengaged to one of the recesses 34, e.g. to that recess which is arranged closest to the dose member spline 35. This is due to the effect of the spring element 4 which biases the dose member 2 towards the distal end 25.

Figure 5:
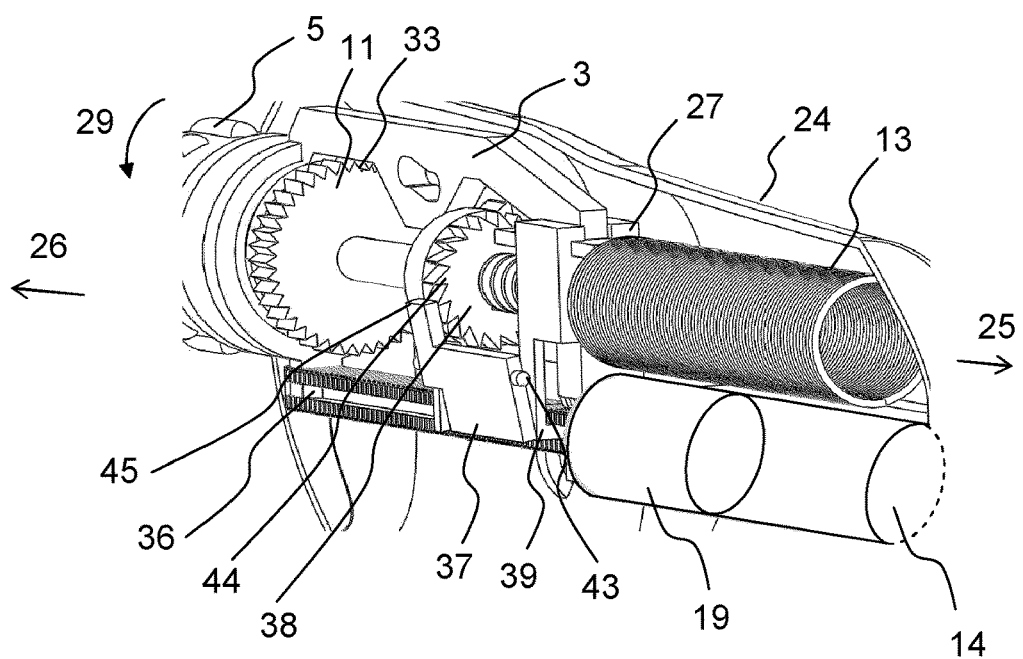
FIG. 5 shows a perspective view of further components of the drug delivery device.

FIG. 5 shows a perspective view of components of the drug delivery device 200 illustrating, e.g. the function of a last dose mechanism of the drug delivery device 200. A last dose ratchet 37 is provisioned to hinder, e.g. a user to set a further dose when the maximum settable dose is already reached or set. When a dose of a drug 31 is set, the drive member 1 moves away from the distal end 25. When a dose is dispensed, the piston rod 6 moves distally with respect to the housing 24 together with the drive member 1. The drive member 1 comprises a drive member arm 39. The last dose ratchet 37 may be borne or retained by the pins 43 which may interact with a further component of the drug delivery device 200 or the housing 24 such that the last dose ratchet 37 is rotated around an axis defined by the pins 43. The dose member 2 comprises a dose member ratchet 38 further comprising teeth 44 which are disposed on a circumferential face or another face. When a large or a maximum number of units has already been dispensed from the drug delivery device 200 and/or when a large or a maximum dose is set, the drive member arm 39 engages a ramp 36 near the proximal end 26. Thereby, the drive member arm 39 is moved radially outwards, thus rotating the last dose ratchet 37 around the axis which extends through the pins 43. Due to the rotation of the last dose ratchet 37, an end portion 45 of the last dose ratchet 37 engages the teeth 44 of the dose member ratchet 38 such that the dose member 2 is prevented from rotation in the first direction 29, i.e. the direction in which the set dose is increased. In the setting mode of operation, the dose member 2 may then be moved in the second direction (cf. arrow 32 in FIG. 1) in order to decrease or cancel the dose. Thereby, the drive member 1 is moved distally with respect to the piston rod 6. When the maximum dose is set, the dose member 2 is thus prevented from being rotated in the first direction 29 to set an additional dose of drug 31.

Figure 6:
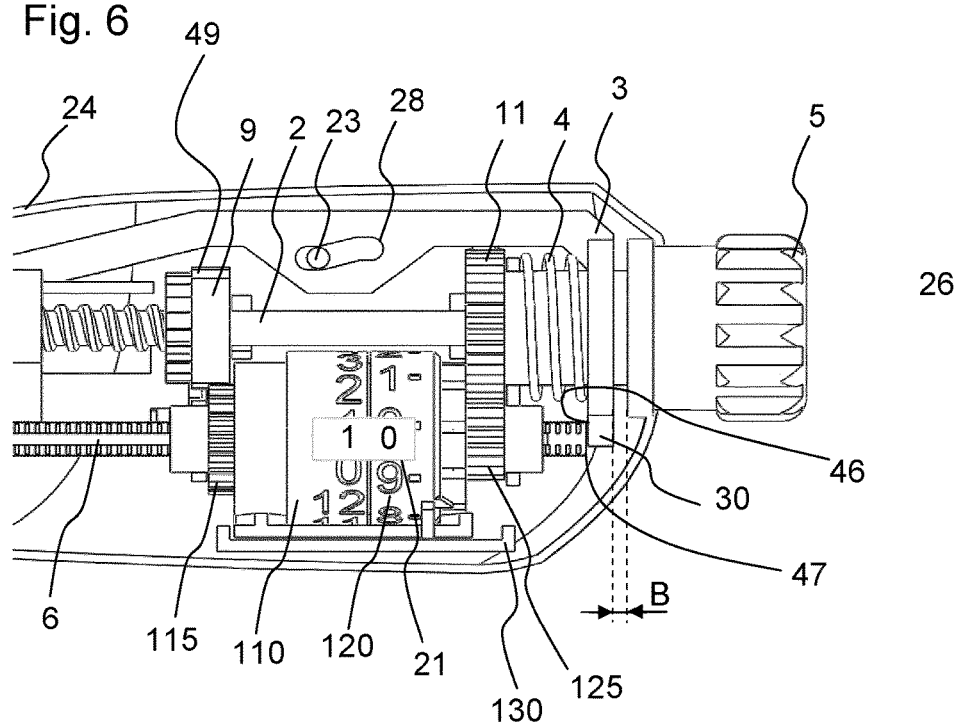
FIG. 6 shows a side view of components of the drug delivery device.
Figure 7:
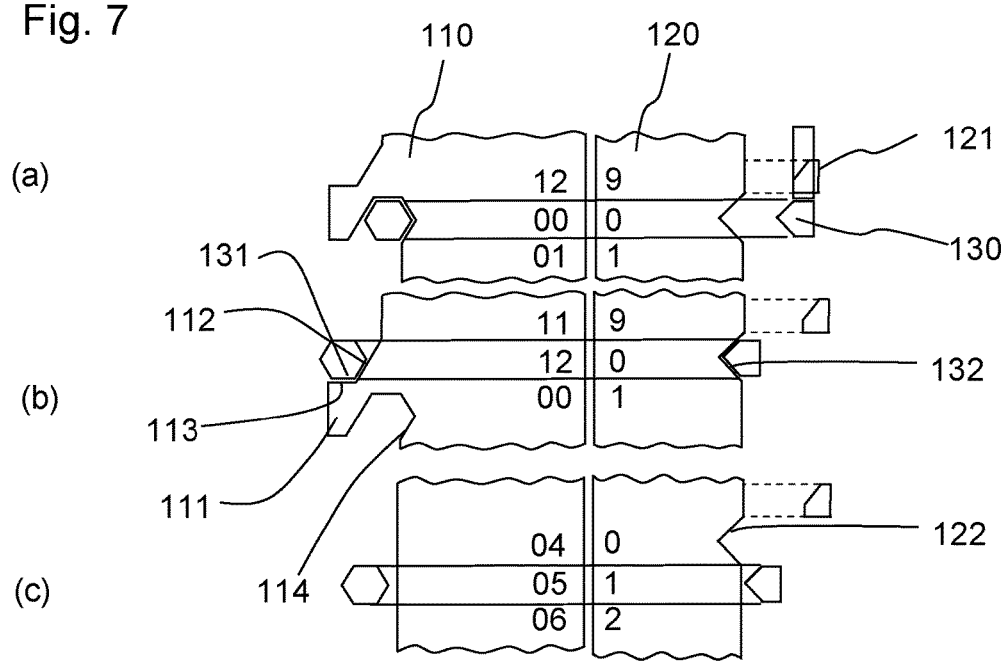
FIGS. 7A to 7C show the schematics of an indication mechanism of the drug delivery device, respectively.

FIG. 6 shows a partial side view of inner components of the drug delivery device 200. In the depicted situation, the drug delivery device 200 is in an initial state and the rod displacement feature 30 abuts or is closely arranged to the piston rod 6. When the dose button 5 is then moved or depressed in the distal direction by a distance B which may correspond to 1 mm, the dose button abuts the displacement member 3. Upon further distal movement of the dose button 5, the displacement member 3 and also the piston rod 6 is moved distally against the resilience of the spring element 4. The indication assembly 100 is shown in FIG. 6 in greater detail. The drug delivery device 200 may comprise a window 21 which may be comprised by the housing 24. The dose member 2 comprises a first pinion 9. The pinion 11 exhibits a second pinion, as mentioned above. The first indication member 110 further comprises a first corresponding pinion 115 which is engaged or engagable to the first pinion 9. The first pinion 9 comprises a protrusion 49. The second indication member 120 further comprises a second corresponding pinion 125 which is engaged to the second pinion 11. The first and the second indication member 110, 120 comprise indication numbers or symbols which, e.g. to indicate the size of a set dose. The first and the second indication members 110, 120 are mechanically decoupled from one another. The dose member 2 may be suitable to drive the first and the second indication member 110, 120, particularly to rotate said components via the first and the second pinion 9, 11 with respect to the housing 24. The first indication member 110 may be incrementally rotatable such that when the dose member 2 is rotated by one revolution, the first indication member 110 is rotated by one increment due to an engagement of the protrusion 49 with the first corresponding pinion 115. The locking member 130 may be rotationally locked with respect to the housing 24 of the drug delivery device 200. Thereby, the housing 24 may be and/or act as a locking member guide. The first and the second indication members 110, 120 are rotatable with respect to the locking member 130. The axis of rotation may be an axis parallel to the longitudinal axis x of the drug delivery device 200. The locking member 130 may be axially movable respect to the housing 24. In FIG. 6, a rotation of the dose member 2 in the first direction would lead to a rotation of the second indication member 120 in the second direction such that the number 1 would be indicated through the window 21. In FIG. 7 the counting direction of the depicted numbers of the first and second indication member 110, 120 is reversed for the sake of clarity.

By means of FIG. 7 the indication assembly 100 is described schematically and in greater detail. The indication assembly 100 may contribute to a display mechanism of the drug delivery device 200 which allows, e.g. for an indication and/or counting of set doses of the drug delivery device 200. The first indication member 110 comprises a first indication feature 111 and the second indication member 120 comprises a second indication feature 122 which may be a recess. The first indication feature 111 comprises a guiding surface 112 and a stop face 113. The locking member 130 comprises a first locking member feature 131 and a second locking member 132. The first indication member 110 further comprises a cut-out 114. The first and the second locking member feature 131, 132 are arranged on opposite sides of the locking member 130. The first and the second indication member 110, 120 are at least partially arranged axially between the first and the second locking member feature 131, 132.

In FIG. 7a, a dose of zero units is indicated. The locking member 130 is arranged in the cut-out 114. Via the cut-out the first indication member 110 is rotationally locked in the second direction with respect to the locking member 130. The second indication member 120 further comprises a second interaction feature or stop 121. The locking member 130 is arranged at an axial position, wherein it abuts the stop 121, thereby simultaneously locking the second indication member 120 rotationally in the second direction with respect to the locking member 130. This situation may correspond to an initial position of the locking member 130, wherein the set dose is zero. The first and the second indication member 110, 120 may comprise cylindrical indication surfaces. The first and the second locking member features 131, 132 comprise one or more even surfaces which are arranged obliquely with respect to the axis of rotation of the first or the second indication member 110, 120. The first and the second indication member 110, 120 may rotate around a common axis, preferably around the longitudinal axis x. When a dose of the drug delivery device 200 is set, the dose member 2 is rotated in the first direction via the dose button 5 such that this set dose may be indicated through the window 21. Such rotation may relate to a rotation of the first and the second indication member 110, 120 in a first rotational direction with respect to the locking member 130. A rotation of the dose member 2 in the second direction relates, accordingly, to a rotation of the first and the second indication member 110, 120 in a second rotational direction with respect to the locking member 130. When a dose of the drug delivery device 200 is set, the second pinion 11, drives the second corresponding pinion 125 of the second indication member 120 such that the set dose, i.e. the dose indicated by the indication assembly 100 increases. Thus, when, in FIG. 7, the indicated dose (which may correspond to the number in the middle) is increased, the indication assembly 100 and the dose member 2 are configured such that, when the second indication member 120 is rotated for one revolution, the first indication member 110 is rotated by an angle corresponding to one digit such that "1" is indicated instead of "0". Thereby, the locking member 130 is moved axially and out of the cut-out 114 of the first indication member 110. Now the locking member 130 is in a non-locking position, as, for example, shown in FIG. 7c by means of the indicated dose of 51 units. The locking member 130 is biased towards said non-locking position by a biasing member (not explicitly indicated) with respect to the first and the second indication members 110, 120. Preferably, the locking member is biased towards the initial position of the locking member 130. When the maximum dose of, for example 120 units, is set (cf. FIG. 7b), which may correspond to a predetermined angle of the first and/or the second indication member 110, 120 with respect to the locking member 130, the first locking member feature 131 interacts with the first interaction feature 111 such that the locking member 130 is displaced into a locking position (cf. FIG. 7b) with respect to the indication member 130, thereby rotationally locking the first and the second indication member 110, 120 with respect to the locking member 130 in the first direction. The displacement of the locking member 130 with respect to the first and the second indication member 110, 120 is an axial displacement, e.g. along the longitudinal axis x of the drug delivery device 200 (cf. FIG. 1). In the second direction, the first and the second indication member 110, 120 are still rotatable with respect to the locking member 130. The rotation in the second direction may relate to an operation of the drug delivery device 200, wherein a dose is decreased or cancelled. The axial displacement of the locking member 130 is guided by the guiding surface 112 such that the second locking member feature 132 is axially displaced into the second indication feature 122. In FIG. 7b, the locking member 130 abuts the stop face 113. Now, the first and the second indication member 110, 120 are rotationally locked in the first direction with respect to the locking member 130. This situation may relate to an indication of the maximum settable dose (cf. "120" in FIG. 7b).

As an advantage of the presented indication assembly, a display or indication mechanism for the drug delivery device can be provided which functions with a low number mutually interacting components and thus the counting assembly can be embodied robust and safe.

An application of the presented indication assembly is not restricted to drug delivery device, but merely illustrated exemplarily by that means.

The end of a dose delivery action may be indicated by a feature (not explicitly indicated) which provides an audible feedback when further components of the drug delivery device move relative to one another.

The drug delivery device may additionally comprise components which are not explicitly indicated and/or the function of which is not described herein. For instance, the presented device may comprise a mechanism which decouples or ratchets the dose button relative to the dose member if an excessive torque is applied to the dose button by the user in the setting mode of operation.

Although this is not explicitly described herein, the actuation member and the displacement member may be embodied in a single component and the whole configuration of the drive mechanism and/or the device may be adjusted accordingly.

A further variant of the design may allow the user to decouple the coupling feature from the piston rod feature such that the piston rod can be moved axially, e.g. proximally, with respect to the housing. This is particularly advantageous when the drug delivery device is configured reusable such that the piston rod can be reset and the cartridge can be changed.

The drive mechanism may further comprise a clutch element which is configured to receive motion of the actuation member when the user attempts to set a dose greater than the maximum settable dose. This may be embodied by means of a torque limiter comprising, e.g. protrusions, recesses and/or resilient elements preventing destruction or damage of components of the drive mechanism and/or the drug delivery device when the user attempts to set a dose greater than the maximum settable dose.

The term "drug" or "substance", as used herein, preferably means a pharmaceutical formulation containing at least one pharmaceutically active compound, wherein in one embodiment the pharmaceutically active compound has a molecular weight up to 1500 Da and/or is a peptide, a protein, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivatives are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39), wherein the group -Lys6-NH2 may be bound to the C-terminus of the Exendin-4 derivative;

or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2, H-Asn-(Glu)5-des Pro36, Pro37, Pro38 [Met(O)14, Asp28] Exendin-4(1-39)-NH2, des Pro36, Pro37, Pro38 [Met(O)14, Asp28] Exendin-4 (1-39)-(Lys)6-NH2, H-(Lys)6-des Pro36, Pro37, Pro38 [Met(O)14, Asp28] Exendin-4(1-39)-(Lys)6-NH2, H-Asn-(Glu)5 des Pro36, Pro37, Pro38 [Met(O)14, Asp28] Exendin-4(1-39)-(Lys)6-NH2, H-Lys6-des Pro36 [Met(O)14, Trp(O2)25, Asp28] Exendin-4(1-39)-Lys6-NH2, H-des Asp28 Pro36, Pro37, Pro38 [Met(O)14, Trp(02)25] Exendin-4(1-39)-NH2, H-(Lys)6-des Pro36, Pro37, Pro38 [Met(O)14, Asp28] Exendin-4(1-39)-NH2, H-Asn-(Glu)5-des Pro36, Pro37, Pro38 [Met(O)14, Trp(O2)25, Asp28] Exendin-4(1-39)-NH2, des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2) 25, Asp28] Exendin-4(S1-39)-(Lys)6-NH2, H-Asn-(Glu)5-des Pro36, Pro37, Pro38 [Met(O)14, Trp (O2)25, Asp28] Exendin-4(1-39)-(Lys)6-NH2;

or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropin (Follitropin, Lutropin, Choriongonadotropin, Menotropin), Somatropin (Somatropin), Desmopressin, Terlipressin, Gonadorelin, Triptorelin, Leuprorelin, Buserelin, Nafarelin, Goserelin.

A polysaccharide is for example a glucosaminoglycan, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystallizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

The scope of protection of the invention is not limited to the examples given hereinabove. The invention is embodied in each novel characteristic and each combination of characteristics, which particularly includes every combination of any features which are stated in the claims, even if this feature or this combination of features is not explicitly stated in the claims or in the examples.

REFERENCE NUMERALS

1 Drive member
2 Dose member
3 Displacement member
4 Spring element
5 Dose button
6 Piston rod
9 First pinion
11 Second pinion
13 Drive spring
14 Cartridge
15 Drive feature
16 Coupling element
17 Piston rod feature
19 Plunger
20 Coupling feature
21 Window
22 Outer thread
23 Guide feature
24 Housing
25 Distal end
26 Proximal end
27 Guidance
28 Bore
29 First direction
30 Rod displacement feature
31 Drug
32 Second direction
33 Clutch feature
34 Recess (dose button)
35 Dose member spline
36 Ramp
37 Last dose ratchet
38 Dose member ratchet
39 Drive member arm
40 Teeth (piston rod)
41 Teeth (coupling element)
42 Teeth (drive feature)
43 Pin
44 Teeth (dose member ratchet)
45 End portion
46 Distal face
47 Proximal face
48 Teeth (second pinion)
49 Protrusion
50 Drive member displacement member
100 Indication assembly
110 First indication member
111 First interaction feature
112 Guiding surface
113 Stop face
114 Cut-out
115 First corresponding pinion
120 Second indication member
121 Second interaction feature
122 Second indication feature/recess
125 Second corresponding pinion
130 Locking member
131 First locking member feature
132 Second locking member feature
200 Drug delivery device
x Longitudinal axis
A,B,D Distance

The invention claimed is:

1. A drive mechanism for a delivery device, the drive mechanism comprising:
a housing having a proximal end and a distal end;
a piston rod having a longitudinal axis and a piston rod feature;
a drive member movable with respect to the housing, the drive member comprising a drive feature, the drive member radially movable between a first position and a second position, wherein the drive feature is selectively engageable with the piston rod feature by a radial displacement of the drive member with respect to the piston rod, the drive mechanism configured such that:
when the drive member is in the first position, the drive member is disengaged from the piston rod and movable with respect to the piston rod, and
when the drive member is in the second position, the drive feature is engaged with the piston rod feature such that, when the drive member moves distally with respect to the housing, a distal movement of the drive member with respect to the housing is transferred to the piston rod such that the piston rod moves distally with respect to the housing; and
a coupling element fixed to or formed integrally with the housing, the coupling element comprising a plurality of axially spaced coupling features each of which is configured to establish a unidirectional coupling with the piston rod feature such that a proximal movement of the piston rod with respect to the housing is prevented, wherein when one of the coupling features establishes the unidirectional coupling, another one of the coupling features does not establish the unidirectional coupling and wherein the coupling features and the piston rod feature are configured such that the unidirectional coupling is formed by different coupling features depending on a relative position of the piston rod and the coupling element.

2. The drive mechanism according to claim 1, wherein the piston rod feature comprises a set of teeth arranged and configured to be engageable with the coupling features.

3. The drive mechanism according to claim 2, wherein each of the coupling features comprises at least one tooth arranged and configured to be engageable with the set of teeth of the piston rod feature and wherein an axial distance between the coupling features is chosen such that a distal end face of the at least one tooth of a first coupling feature of the coupling features abuts a proximal end face of a first tooth of the set of teeth of the piston rod feature and a distance D between a distal end face of the at least one tooth of a second coupling feature of the coupling features and a proximal end face of a second tooth of the set of teeth of the piston rod feature is smaller than a distance A between proximal end faces of two adjacent teeth of the set of teeth of the piston rod feature.

4. The drive mechanism according to claim 3, wherein the drive mechanism is configured such that, when the piston rod is moved distally by the distance D with respect to the housing, the first tooth of the piston rod feature is moved out of abutment with the at least one tooth of the first coupling feature and the proximal end face of the second tooth of the piston rod feature abuts the distal end face of the at least one tooth of the second coupling feature, wherein the distance D corresponds to a minimum amount of substance which can be dispensed from the delivery device.

5. The drive mechanism according to claim 1, wherein the drive feature comprises a plurality of axially spaced drive features and each drive feature comprises at least one tooth configured and arranged to be engageable with a set of teeth of the piston rod feature, wherein the drive features and the piston rod feature are arranged and configured such that when the drive member is in the second position, a distal end face of the at least one tooth of one of the drive features abuts a proximal end face of a tooth of the piston rod feature and a distal end face of the at least one tooth of another one of the drive features is spaced by a distance D' from a proximal end face of another tooth of the piston rod feature, wherein the distance D' corresponds to a minimum amount of substance which can be dispensed from the delivery device.

6. The drive mechanism according to claim 1, comprising a dose member, wherein the drive mechanism is configured such that in a setting mode of operation, the drive member is in the first position and in a dispensing mode of operation, the drive member is in the second position, wherein in the setting mode of operation, the dose member is rotatable in a first direction with respect to the housing to set a dose and in the dispensing mode of operation, the dose member is rotatable in a second direction opposite to the first direction with respect to the housing to dispense a set dose.

7. The drive mechanism according to claim 6, wherein the drive mechanism is configured such that a rotation of the dose member with respect to the housing is converted into an axial movement of the drive member with respect to the piston rod.

8. The drive mechanism according to claim 6, wherein the dose member and the drive member are threadedly coupled to each other.

9. The drive mechanism according to claim 6, comprising a drive spring which is coupled to the dose member, the drive spring arranged and configured such that, when the dose member rotates in the first direction with respect to the housing, the drive spring is loaded and wherein in the dispensing mode of operation, the drive spring drives a rotation of the dose member in the second direction with respect to the housing.

10. The drive mechanism according to claim 9, comprising a releasable clutch mechanism, wherein the releasable clutch mechanism is configured such that, in the setting mode of operation, the releasable clutch mechanism is engaged and the dose member is selectively rotationally locked with respect to the housing against a spring force of the drive spring and, in the dispensing mode of operation, the releasable clutch mechanism is released and the dose member is rotated by the drive spring with respect to the housing.

11. The drive mechanism according to claim 6, comprising an actuation member and a displacement member, wherein the actuation member is configured to interact with the displacement member such that, when in the setting mode of operation, an axial movement of the actuation member is transferred to a radial movement of the displacement member with respect to the piston rod, the drive mechanism is switched from the setting mode of operation to the dispensing mode of operation, whereby the drive member moves from the first position to the second position.

12. The drive mechanism according to claim 11, comprising a guide feature which is axially fixed to or formed integrally with the housing, wherein the guide feature and the displacement member are arranged and configured such that an axial movement of the displacement member with respect to the housing is at least partially converted into a radial movement of the displacement member with respect to the piston rod, wherein the displacement member interacts with the drive member such that, when the displacement member moves radially with respect to the piston rod, the drive member is displaced with respect to the piston rod from the first position to the second position.

13. The drive mechanism according to claim 10, wherein a displacement member is rotationally locked with respect to the housing and the displacement member comprises a clutch feature which is part of the releasable clutch mechanism, wherein in the setting mode of operation, the displacement member is axially moved with respect to the dose member, thereby releasing the releasable clutch mechanism.

14. Drug A drug delivery device comprising:
a drive mechanism comprising:
a housing having a proximal end and a distal end;
a piston rod having a longitudinal axis (x) and a piston rod feature;
a drive member movable with respect to the housing, the drive member comprising a drive feature, the drive member radially movable between a first and a second position, wherein the drive feature is selectively engageable with the piston rod feature by a radial displacement of the drive member with respect to the piston rod, the drive mechanism configured such that:
when the drive member is in the first position, the drive member is disengaged from the piston rod and movable with respect to the piston rod, and
when the drive member is in the second position, the drive feature is engaged with the piston rod feature such that, when the drive member moves distally with respect to the housing, a distal movement of the drive member with respect to the housing is transferred to the piston rod such that the piston rod moves distally with respect to the housing; and
a coupling element fixed to or formed integrally with the housing, the coupling element comprising a plurality of axially spaced coupling features each of which is configured to establish a unidirectional coupling with the piston rod feature such that a proximal movement of the piston rod with respect to the housing is prevented, wherein when one of the coupling features establishes the unidirectional coupling, another one of the coupling features does not establish the unidirectional coupling and wherein the coupling features and the piston rod feature are configured such that the unidirectional coupling is formed by different coupling features depending on a relative position of the piston rod and the coupling element.

15. A drive mechanism for a delivery device, the drive mechanism comprising:
a housing having a proximal end and a distal end;
a piston rod having a longitudinal axis and a piston rod feature; and
a drive member movable with respect to the housing, the drive member comprising a drive feature, the drive member radially movable between a first position and a second position, wherein the drive feature is selectively engageable with the piston rod feature by a radial displacement of the drive member with respect to the piston rod, the drive mechanism configured such that:

when the drive member is in the first position, the drive member is disengaged from the piston rod and movable with respect to the piston rod, and when the drive member is in the second position, the drive feature is engaged with the piston rod feature such that, when the drive member moves distally with respect to the housing, a distal movement of the drive member with respect to the housing is transferred to the piston rod such that the piston rod moves distally with respect to the housing, wherein the drive feature comprises a plurality of axially spaced drive features and each drive feature comprises at least one tooth configured and arranged to be engageable with a set of teeth of the piston rod feature, wherein the drive features and the piston rod feature are arranged and configured such that when the drive member is in the second position, a distal end face of the at least one tooth of one of the drive features abuts a proximal end face of a tooth of the piston rod feature and a distal end face of the at least one tooth of another one of the drive features is spaced by a distance D' from a proximal end face of another tooth of the piston rod feature, wherein the distance D' corresponds to a minimum amount of substance which can be dispensed from the delivery device.

* * * * *

UNITED STATES PATENT AND TRADEMARK OFFICE
CERTIFICATE OF CORRECTION

PATENT NO. : 10,441,724 B2
APPLICATION NO. : 14/904736
DATED : October 15, 2019
INVENTOR(S) : Tom Oakley, Matt Schumann and Stuart Milne Page 1 of 1

It is certified that error appears in the above-identified patent and that said Letters Patent is hereby corrected as shown below:

In the Claims

Column 21, Line 42, Claim 9, delete "loaded" and insert -- loaded, --.

Column 22, Line 18, Claim 14, before "A drug", delete "Drug".

Column 22, Line 21, Claim 14, delete "axis (x)" and insert -- axis --.

Signed and Sealed this
Fourteenth Day of January, 2020

Andrei Iancu
*Director of the United States Patent and Trademark Office*